United States Patent
Carson et al.

(10) Patent No.: US 8,696,981 B2
(45) Date of Patent: *Apr. 15, 2014

(54) APPARATUS AND METHODS FOR DISINFECTING SPACES

(75) Inventors: William W. Carson, Hopkinton, MA (US); Paul Sabin, Needham, MA (US); Thomas J. Dee, Holliston, MA (US)

(73) Assignee: TBS Technologies, LLC, Holliston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/595,278

(22) Filed: Aug. 27, 2012

(65) Prior Publication Data

US 2013/0189153 A1 Jul. 25, 2013

Related U.S. Application Data

(63) Continuation of application No. 13/087,576, filed on Apr. 15, 2011, now Pat. No. 8,262,986, which is a continuation of application No. PCT/US2009/061098, filed on Oct. 16, 2009.

(60) Provisional application No. 61/105,991, filed on Oct. 16, 2008.

(51) Int. Cl.
*A61L 2/24* (2006.01)
*A61L 2/18* (2006.01)

(52) U.S. Cl.
USPC .................................. 422/3; 422/105; 422/37

(58) Field of Classification Search
USPC ............................................ 422/4, 37, 105, 3
See application file for complete search history.

(56) References Cited

U.S. PATENT DOCUMENTS

| | | | |
|---|---|---|---|
| 4,335,075 A | 6/1982 | Kackos | |
| 5,360,372 A | 11/1994 | Newman et al. | |
| 6,217,441 B1 * | 4/2001 | Pearman et al. | 454/333 |
| 6,235,240 B1 | 5/2001 | Heredia et al. | |
| 7,264,773 B2 * | 9/2007 | Adiga et al. | 422/28 |
| 7,534,398 B2 | 5/2009 | Dee et al. | |
| 2001/0053667 A1 | 12/2001 | Kreichauf | |
| 2003/0101700 A1 * | 6/2003 | Burdine et al. | 55/385.2 |

(Continued)

OTHER PUBLICATIONS

Extended European Search Report for EP Appliction No. EP 09 82 1368 dated May 15, 2012.

(Continued)

*Primary Examiner* — Kevin Joyner
(74) *Attorney, Agent, or Firm* — McCarter & English, LLP; Jonathan M. Sparks; Colleen H. Witherell

(57) ABSTRACT

The instant invention provides methods and apparatus for disinfecting a space, e.g., a hospital room, using chlorine dioxide. One aspect of the invention provides an apparatus for disinfecting a space. The apparatus includes: a chlorine dioxide gas generator; a sensor adapted and configured to measure the relative pressure inside the space and outside the space; and a computer operatively connected to the sensor and the chlorine dioxide generator, the computer adapted and configured to control the chlorine dioxide generator to operate only when the space is under negative pressure as compared to outside the space. Another aspect of the invention provides a method of disinfecting a space. The method includes: setting an apparatus as described herein in the space; and allowing the apparatus to determine if the space is under negative pressure. If the space is under negative pressure, the apparatus generates chlorine dioxide gas to disinfect the space.

29 Claims, 9 Drawing Sheets

(56) References Cited

U.S. PATENT DOCUMENTS

| | | |
|---|---|---|
| 2004/0047776 A1* | 3/2004 | Thomsen ............... 422/186.07 |
| 2005/0019210 A1 | 1/2005 | Rosenblatt et al. |
| 2005/0084415 A1 | 4/2005 | McVey et al. |
| 2005/0220662 A1 | 10/2005 | Hedman |
| 2006/0261188 A1* | 11/2006 | Ito et al. ..................... 239/306 |
| 2008/0139869 A1 | 6/2008 | Wilson et al. |
| 2008/0292507 A1 | 11/2008 | Dee et al. |
| 2009/0081310 A1 | 3/2009 | Mason |

OTHER PUBLICATIONS

International Preliminiary Report on Patentability for International Application PCT/US2009/061098 (Apr. 19, 2011).

Written Opinion of the International Searching Authority, International Application PCT/US09/61098 (Dec. 23, 2009).

International Search Report, International Application PCT/US09/61098 (Dec. 23, 2009).

* cited by examiner

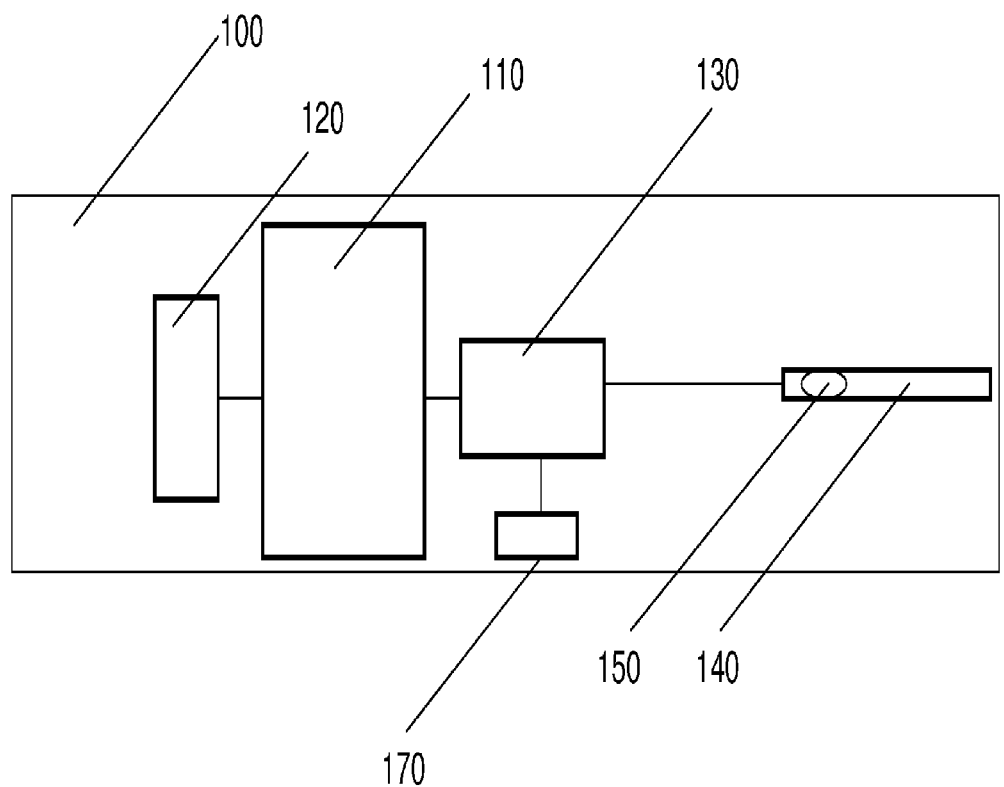

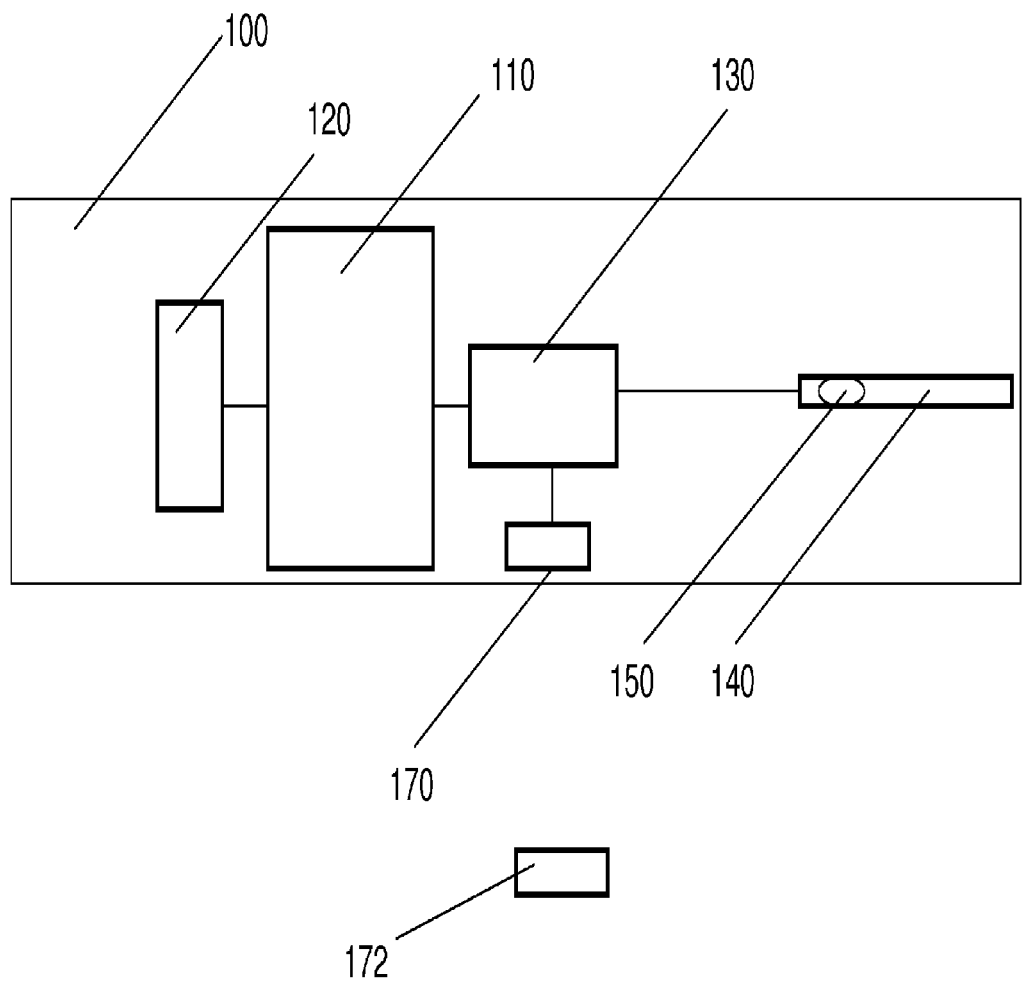

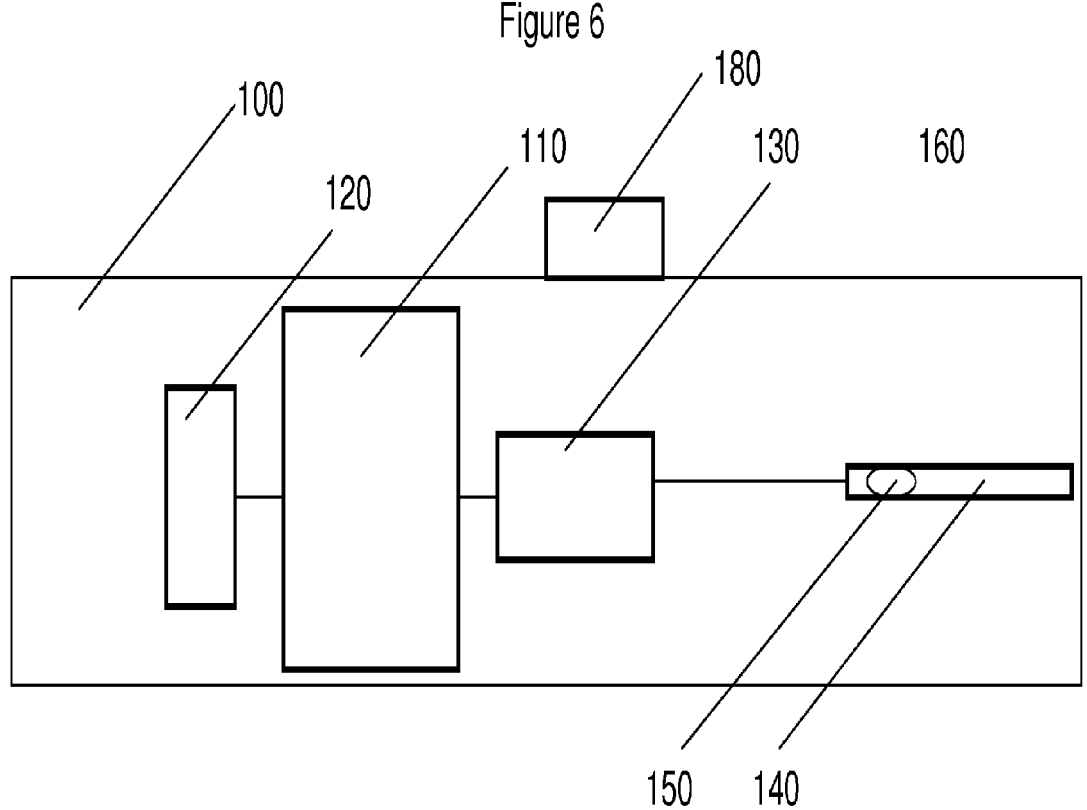

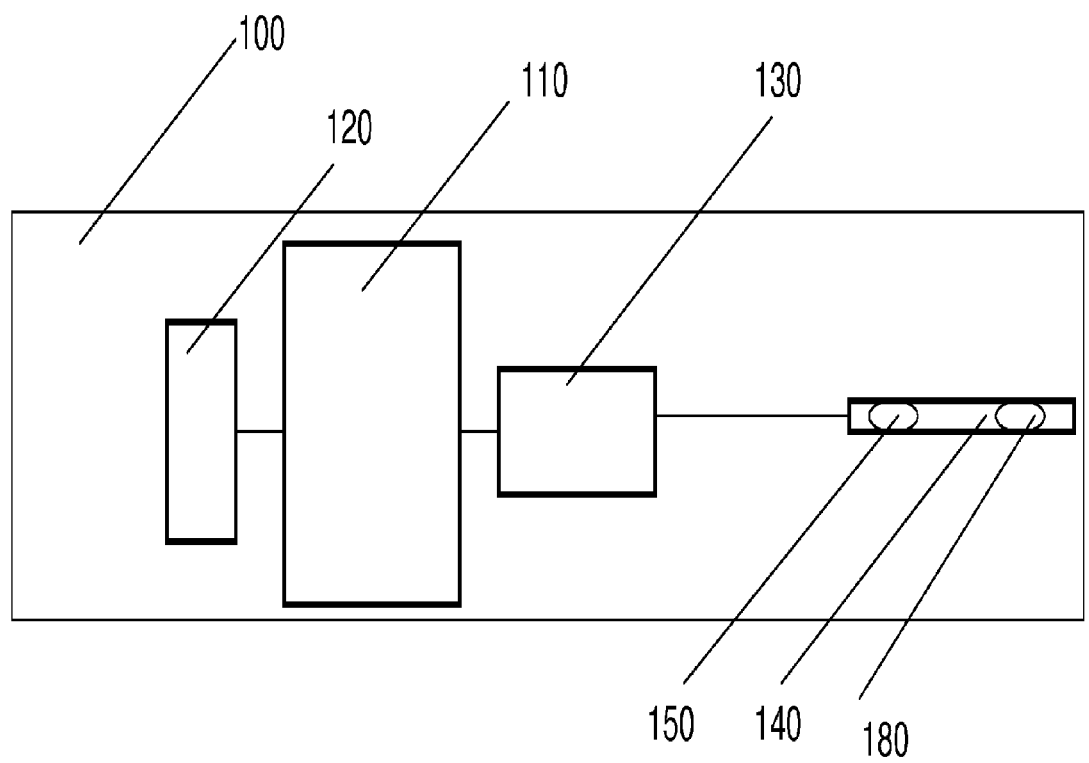

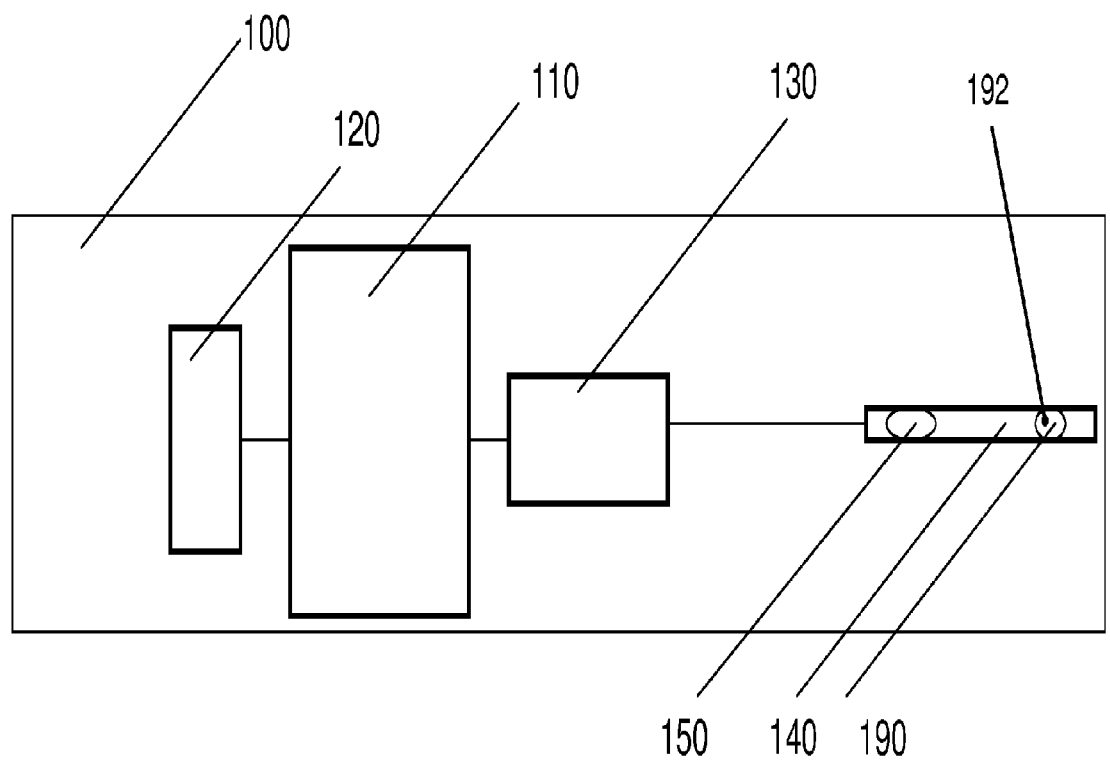

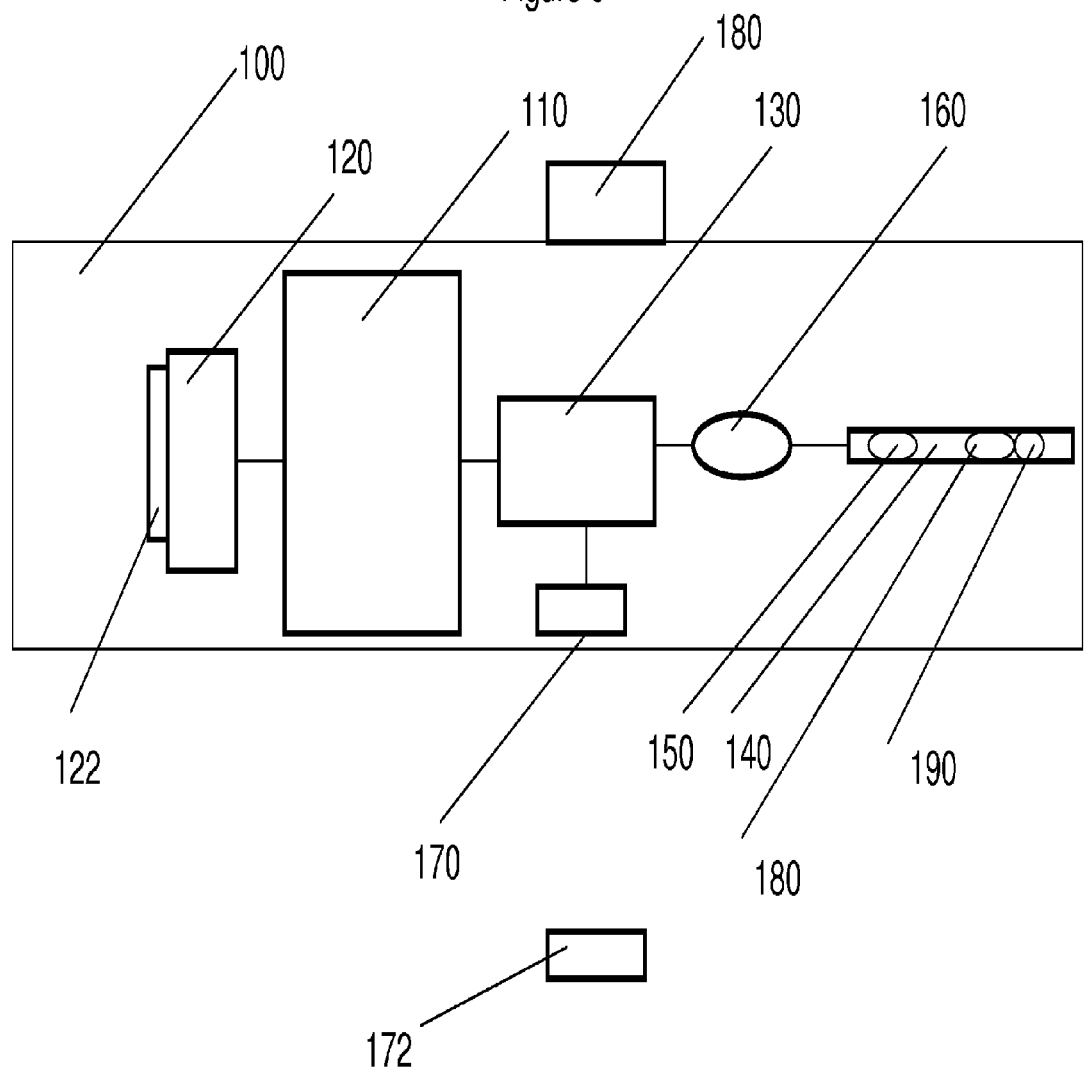

APPARATUS AND METHODS FOR DISINFECTING SPACES

CROSS-REFERENCE TO RELATED APPLICATIONS

This application is a continuation of U.S. patent application Ser. No. 13/087,576, filed Apr. 15, 2011, allowed, which is a continuation of International Application No. PCT/US2009/061098, filed Oct. 16, 2009, which claims the benefit of U.S. Provisional Patent Application No. 61/105,991, filed Oct. 16, 2008. The entire contents of the aforementioned applications are hereby incorporated by reference.

BACKGROUND OF THE INVENTION

Chlorine dioxide was discovered in the early 1800's, and was adopted by commerce in the United States in the 1940's. Chlorine dioxide has been called the ideal biocide and the ability of chlorine dioxide to reduce or eliminate viable microbes, e.g., bacteria, viruses, fungi, mold spores, algae and protozoa, is well-documented and well known. See, for example, Franklin, C. L. et al. (1991) *Am Vet Med Assoc* 198:1625-30; Korich K. G., et al. (1990) *Appl Environ Microbiol.* 56:1423-8; Boddie et al. (2000) *J Dairy Sci.* 83:2975-9; Lee et al. (2004) *J Food Prot.* 67:1371-6; Han et al. (2003) *J Environ Health* 66:16-21; Sy et al. (2005) *J Food Prot.* 68:1176-87; and LeChevallier M. W. et al. (1988) *Appl Environ Microbiol.* 54:2492-9.

Chlorine dioxide inactivates microorganisms by oxidizing key components of a microorganism's membrane proteins that are vital to the membrane's structure and function. Also, the oxidizing reaction that causes microorganism inactivation does not form trihalomethanes (THMs) or haloacetic acids (HAAs).

Approvals and registrations for use of chlorine dioxide in a wide variety of applications have been granted by the EPA, FDA and USDA, and such approvals and registrations have led to an increasing adoption of the use of chlorine dioxide.

There are many reasons for the ongoing expansion of chlorine dioxide use including its effectiveness against microorganisms at very low concentrations.

A major limitation to the use of chlorine dioxide is that chlorine dioxide can not be manufactured in bulk at an industrial gas plant and shipped to final use destinations. Accordingly, chlorine dioxide must be generated on-site.

Moreover, the rate of hospital-acquired infection is increasing and the use of chlorine dioxide to disinfect spaces, such as hospital rooms, would be beneficial to reduce the number of hospital-acquired infections. However, the use of chlorine dioxide gas in public spaces has limitations that are not addressed by the prior art.

Accordingly, the instant invention provides methods and apparatus for the disinfection of spaces, e.g., hospital rooms or nursing home rooms.

SUMMARY OF THE INVENTION

The instant invention provides methods and apparatus for disinfecting spaces. In a particular embodiment, the invention provides methods and apparatus for safely disinfecting a hospital room or nursing home room using chlorine dioxide gas.

In one aspect, the instant invention provides an apparatus for disinfecting a space, comprising, a chlorine dioxide gas generator operatively connected to a sensor; wherein the sensor measures the relative pressure inside the space and outside the space and allows the chlorine dioxide gas generator to operate when the space is under negative pressure as compared to outside the space, and a computer, wherein the apparatus is under the control of a computer.

In one embodiment, the apparatus further comprises a device for sealing the space under the door or for sealing a doorway. In another embodiment, the device for sealing the space under the door or for sealing a doorway comprises a pressure sensor. In another embodiment, the device for sealing the space under the door or for sealing the doorway comprises an inflatable bladder, an inflatable door that fits into the door frame, a compressible foam insert for under the door, or a sheet that covers the outside of the door. In certain embodiments of the invention the apparatus may include two or more devices for sealing the space under a door or for sealing the doorway.

In one embodiment, the apparatus further comprises a compressor, wherein the compressor inflates the bladder thereby sealing the space under the door.

In another embodiment, the apparatus further comprises a first chlorine dioxide gas sensor. In one embodiment, the chlorine dioxide gas sensor turns off the generator when a preset level of chlorine dioxide gas is obtained. Exemplary levels of chlorine dioxide comprise the various levels between 5 ppm minutes and 50,000 ppm minutes. In a specific embodiment, the level is about 300 ppm minutes.

In another embodiment, the preset chlorine dioxide gas level is maintained for a preset time, e.g., 10 or 15 minutes. In another embodiment, the apparatus comprises a second chlorine dioxide gas sensor. In specific embodiments, the second chlorine dioxide gas sensor operates remotely from the apparatus.

In another embodiment, when the first and second chlorine dioxide gas sensors indicate a sufficient level of chlorine dioxide gas for a sufficient time, the sensors signal the computer to turn off the generator. In an exemplary embodiment, the level is 300 ppm minutes as sensed by both chlorine dioxide gas sensors. For example, this can be 20 minutes of exposure to 15 ppm chlorine dioxide, or any combination that results in 300 ppm minutes of exposure.

In another embodiment, the apparatus further comprises an air circulating device. For example, the air circulating device can be a fan, blower or the like. In one embodiment, the air circulating device circulates the chlorine dioxide gas within the space.

In another embodiment, the apparatus further comprises a chlorine dioxide removal apparatus. For example, the chlorine dioxide removal apparatus can be a filter, e.g., an activated charcoal filter. The chlorine dioxide removal apparatus can be activated or placed in the appropriate position to remove chlorine dioxide form the air once the space has been exposed to a sufficient amount of chlorine dioxide.

In one embodiment, the chlorine dioxide generator generates gaseous chlorine dioxide that is at least 90% pure.

In a specific embodiment, the space to be disinfected is a hospital room or a nursing home room.

In another embodiment, the device for sealing the door also prevents the door from opening.

In another embodiment, the apparatus further comprises a visual indicator that indicates when it is safe to enter the room.

In another embodiment, the apparatus further comprises a visual indicator of the negative pressure.

In another aspect, the invention provides methods of disinfecting a space using the any one of the apparatus described herein. Specifically, the methods include setting the apparatus in the space, preparing the space, and allowing the apparatus to determine if the space is under negative pressure, wherein, if the space is under negative pressure, the apparatus generates chlorine dioxide gas to disinfect the space.

In one embodiment, the space is a hospital room or a nursing home room. In another embodiment, the methods further comprise prevalidating the space. In exemplary embodiments, the prevalidation comprises sealing one or more of the HVAC ducts, electrical outlets, or electronics.

In an exemplary embodiment, the space is exposed to 300 ppm minutes of chlorine dioxide. In a related embodiment, once the space is exposed to a sufficient amount of chlorine dioxide, the apparatus begins filtering the air in the space until the level of chlorine dioxide gas is at or below 0.10 ppm.

In another embodiment, the device for sealing the door unseals once the level of chlorine dioxide is at or below 0.10 ppm.

In another embodiment, the methods of the invention reduce the viable microorganism population by at least 90%. In further embodiments of the invention, the methods of the invention reduce the viable microorganism population by at least 95%, 98%, 99%, 99.9% or more. Exemplary microorganisms include bacteria, viruses, fungi, mold spores, algae and protozoa. Exemplary bacteria include those from the genus *Pseudomonas, Staphylococcus, Escherichia*, or *Enterococcus*.

In another embodiment, the methods of the invention are complete in three hours or less. In one embodiment of the invention, the methods are complete in one hour or less.

In another embodiment, the methods of the invention further comprise validating the disinfection of the space.

BRIEF DESCRIPTION OF THE FIGURES

FIG. 4 depicts the apparatus of FIG. 1, further comprising a sensor for determining chlorine dioxide gas exposure.

FIG. 5 depicts the apparatus of FIG. 1, further comprising a second sensor for determining chlorine dioxide gas exposure. The second sensor operates remotely from the apparatus.

FIG. 6 depicts the apparatus of FIG. 1, further comprising a visual signal attached to the apparatus that validates the disinfection of the space.

FIG. 7 depicts the apparatus of FIG. 1, further comprising a visual signal attached to device for sealing the door that validates the disinfection of the space.

FIG. 8 depicts the apparatus of FIG. 1, further comprising a negative pressure pump.

FIG. 9 depicts the apparatus of FIG. 1, further comprising additional elements represented in FIGS. 2-8.

DETAILED DESCRIPTION

Figure 1:
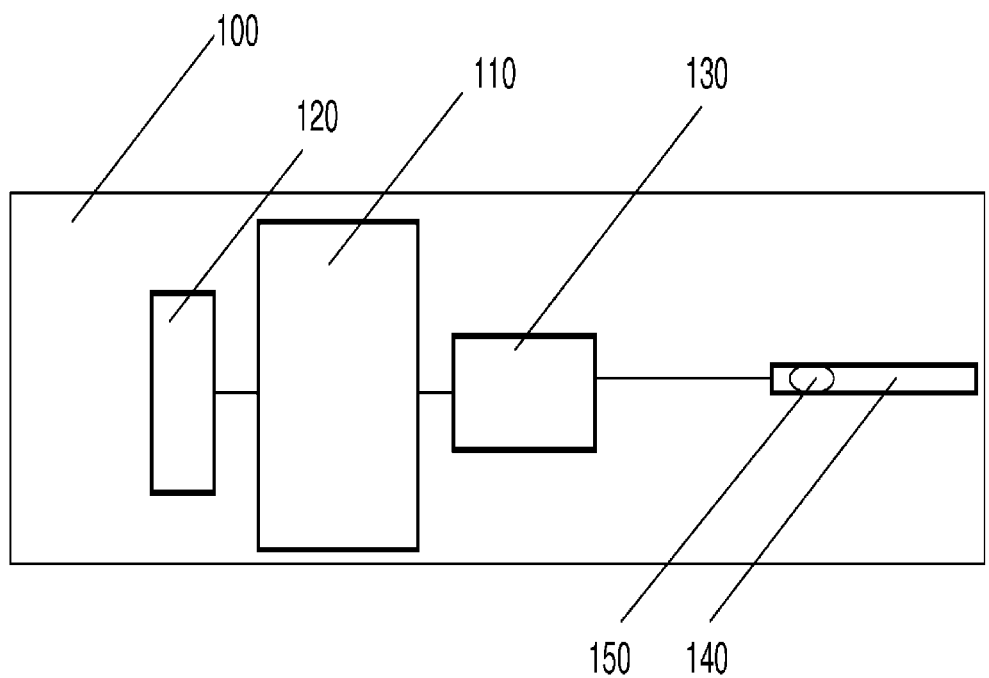
FIG. 1 depicts an apparatus of the invention comprising an air circulating device, a chlorine dioxide gas generator, a computer and a device for sealing a doorway or the space under the door comprising a negative pressure sensor.

The instant invention provides methods and apparatus for the disinfection of spaces, e.g., hospital rooms.

In exemplary embodiments, the invention utilizes chlorine dioxide gas generators described in, for example, U.S. Pat. No. 7,534,398, U.S. Patent Application Publication No. 2008/0292507, and International Application No. PCT/US2009/49924, all of which are assigned to the assignee of the instant invention. These previously-described chlorine dioxide gas generators are modified to allow for use in a hospital room. For example, they have been modified to allow the room to be placed under negative pressure to ensure the safety of people in the hospital.

Exemplary chlorine dioxide gas generators of the invention comprise a system for generation of chlorine dioxide gas comprising a removable cartridge containing the precursor chemicals necessary to produce chlorine dioxide, and a power source, an apparatus for sealing a door, an air circulating device (e.g., a fan), and one or more sensors including a negative pressure sensor.

The power source may be either external to the generator or may be contained within the generator. In one exemplary embodiment, the generator is configured to draw power through an electrical cord attached to a wall socket, as is known in the art. In another exemplary embodiment, the generator is configured to draw electricity from a battery or battery pack housed within or connected to the generator. In one exemplary embodiment, the generator is completely self-contained and portable, meaning that all necessary components are each contained within the generator. In specific embodiments, the power supply is an uninterruptible power supply.

In one exemplary embodiment, the generator includes a detachable display that communicates information about the gas generation cycle, including the length of the cycle, concentration of gas present, validation of treatment, and an indication of whether it is safe to enter the space where generator is being used. The detachable display may completely disconnect from the generator or may be in wired or wireless communication with the generator. Alternatively, the display may be contained within the apparatus for sealing the door.

The removable cartridge is configured to interface with the generator and be quickly and easily replaced. The cartridge may include one or more precursor chemicals that can be combined to produce chlorine dioxide. The cartridge may contain machine-readable identification information to ensure that the cartridge is appropriate for the generator and may confer to the generator information about run time, concentration, etc. One could envision different cartridges for different size rooms. In this case, different cartridges would comprise different amounts of the necessary precursor chemicals. Identification information may be stored or transmitted in a variety of ways, including by way of a bar code or other optical code, in a memory device, or in a radio frequency identification (RFID) chip.

The precursor chemicals housed within the cartridge may be in dry form or aqueous form. Precursor chemicals may be stored within the cartridge in numerous ways, including the following: dry powder form, dry powder mixed together in a tea-bag structure, dry powder separated into two tea-bag structures, dry powder separated into two membrane structures, dry powder mixed together in a dissolvable (water soluble) film bag, dry powder separated into two dissolvable (water soluble) film bags, dry powder mixed together in a dissolvable (water soluble) gel tablet, dry powder separated into two dissolvable (water soluble) gel tablets, dry powder separated into two dry pills and two or more separate compartments. In cases where a precursor chemical containing structure is made from a hydrophilic heat-sealable material, such material may be made with a sufficiently small pore size that it will provide some containment of undesirable residuals.

In certain embodiments precursor chemicals are an acid and a chlorite salt. Exemplary chlorite salts are sodium chlorite, lithium chlorite, barium chlorite, calcium chlorite, magnesium chlorite, or potassium chlorite. Exemplary acids are boric acid, tartaric acid, lactic acid, maleic acid, malic acid, glutaric acid, adipic acid, acetic acid, formic acid, sulfamic acid, sulfuric acid, hydrochloric acid, phosphoric acid, phosphoric anhydride, a sulfuric anhydride and citric acid. An exemplary chlorite salt/acid combination used in the apparatus of the invention is sodium chlorite and citric acid.

In one exemplary embodiment, chlorine dioxide gas is generated within the cartridge and vented directly to the space that is to be decontaminated, e.g., a hospital room or a nursing home room. This gas is then circulated around the room by a fan, blower or other air circulating device.

In certain embodiments, the cartridge may also include a chemical for neutralizing a reaction or the products of a reaction. For example, an ascorbate salt, such as sodium ascorbate, may be combined with the residual chlorine dioxide gas to neutralize the chlorine dioxide. In certain cases, it may be desirable to neutralize various chemicals in the cartridge, either to control the reaction rate or to make the cartridge easier to dispose of or safer to handle. For example, sodium ascorbate will react with chlorine dioxide gas to produce products which are more readily disposed of than chlorine dioxide gas alone. In certain embodiments the neutralizing agent may have a detectable color.

The apparatus of the invention may further comprise an apparatus that effectively seals a door or doorway thereby restricting the flow of chlorine dioxide gas out of the room being treated. By sealing the door to a room, the room can be placed under negative pressure. Exemplary ways to seal a door include a bladder that fits under the door or within a door frame and can be inflated so as to seal the space. In this case, the apparatus of the invention would include a small pump to inflate the bladder. The bladder may be designed to prevent the door from opening. Additionally, compressible material can be inserted under the door to seal this space. An exemplary material is compressible foam. Alternatively, a device or material may be placed on the outside of the door frame, thereby sealing the door.

In specific embodiments of the invention, any of the above-described door sealing apparatus may further include a sensor that measures the relative pressure on each side of the apparatus, i.e., inside the room and in the hallway, and provides a visual indicator when the room is under negative pressure and therefore, when it is safe to begin the disinfection process. Moreover, for safety reasons, this sensor may be connected to the computer controlling the chlorine dioxide gas generating apparatus so that the generation of gas can not begin until the room is under negative pressure. In another embodiment, there can be a second pressure sensor to measures bladder pressure to ensure the door is both locked and sealed.

In order to achieve negative pressure inside the space, a negative pressure pump may be used. In certain embodiments, the negative pressure pump is a stand alone unit. In other embodiments, the negative pressure pump is integrated into the apparatus. In a specific embodiment, the negative pressure pump is integrated into the device for sealing a doorway or the space under the door. A stand-alone unit can pump air out a window, whereas an integrated pump will have to pump air into the hallway or into the HVAC system of the building. The pumps or vents can optionally comprise a device for removing chlorine dioxide gas such as the filters described herein.

Reference will now be made in detail to the present embodiments of the invention, examples of which are illustrated in the accompanying drawings. The apparatus and methods described in this disclosure may be used for producing chlorine dioxide gas useful for disinfecting spaces, including rooms at medical facilities such as hospital rooms.

FIG. 1 depicts an exemplary apparatus of the invention. Apparatus 100 comprises chlorine dioxide gas generator 110, air circulating device 120, computer 130, and a device for sealing a doorway or the area under a door 140. Device 140 can be an inflatable bladder, compressible material such as foam, or a device that attaches to the door frame and creates a seal. Device 140 comprises pressure sensor 150 that determines if the space to be treated is under negative pressure. Apparatus 100 is controlled by computer 130 (which can also be a microprocessor). Computer 130 is operatively connected to sensor 150. When sensor 150 indicates that the space is under negative pressure, computer 130 signals chlorine dioxide gas generator 110 to begin producing chlorine dioxide gas and air circulating device 120 to turn on. In certain embodiments, if during the operation of the apparatus, sensor 150 determines that the room is not under negative pressure, computer 130 signals to chlorine dioxide gas generator 110 to turn off.

Figure 2:
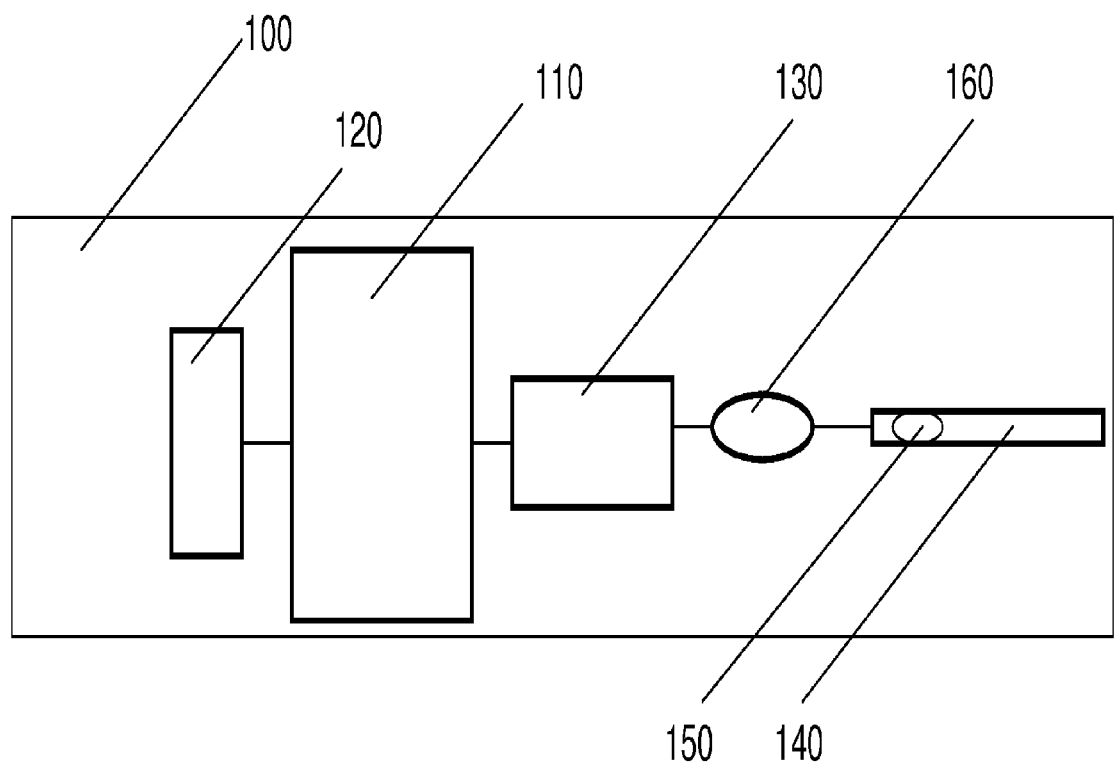
FIG. 2 depicts the apparatus of FIG. 1, further comprising a compressor for inflating the device for sealing a doorway or the space under the door.

FIG. 2 depicts an exemplary apparatus of the invention. As depicted in FIG. 2, apparatus 100 further comprises compressor 160 that inflates device 140, e.g., an inflatable bladder.

Figure 3:
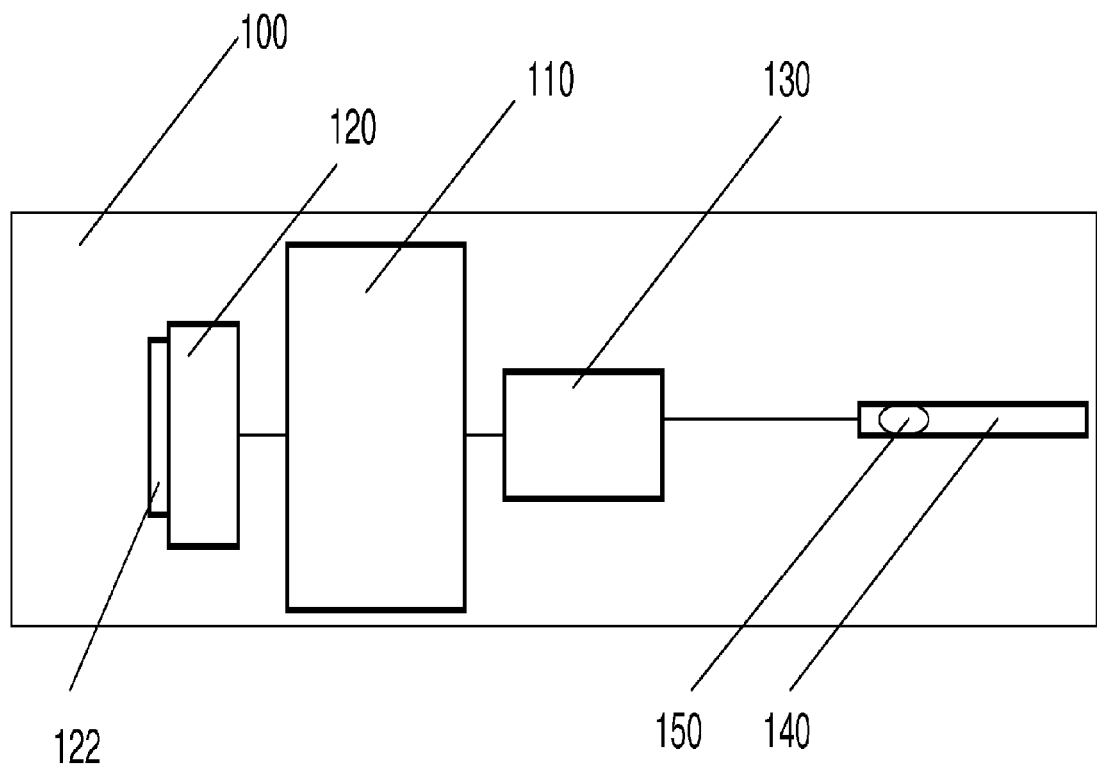
FIG. 3 depicts the apparatus of FIG. 1, further comprising a device for removing the chlorine dioxide gas from the air.

FIG. 3 depicts an exemplary apparatus of the invention. As depicted in FIG. 3, apparatus 100 further comprises chlorine dioxide gas removal device 122. The chlorine dioxide gas removal apparatus may be a filter, e.g., a filter that comprises activated charcoal, or a HEPPA filter containing sodium bisulfite or sodium sulfite. The chlorine dioxide gas removal apparatus 122 can be engaged once the space has been exposed to a sufficient level of chlorine dioxide gas. For example, the chlorine dioxide gas removal apparatus 122 can be placed next to air circulating device 120 thereby circulating air through the device thereby removing chlorine dioxide gas from the air.

FIG. 4 depicts an exemplary apparatus of the invention. As depicted in FIG. 4, apparatus 100 further comprises chlorine dioxide gas sensor 170 operatively connected to computer 130. Sensor 170 measures the level of chlorine dioxide gas in the air and communicates with computer 130. When sufficient levels of chlorine dioxide gas are achieved, computer 130 signals chlorine dioxide gas generator 110 to turn off.

FIG. 5 depicts an exemplary apparatus of the invention. As depicted in FIG. 5, the apparatus of the invention further comprises a second chlorine dioxide gas sensor 172 that operates remotely from apparatus 100. Sensor 172 can communicate with computer 130 remotely. Computer 130 receives input from sensor 170 and sensor 172 and turns off chlorine dioxide gas sensor 110 when both sensors indicate a sufficient exposure to chlorine dioxide gas.

FIG. 6 depicts an exemplary apparatus of the invention. As depicted in FIG. 6 apparatus 100 comprises visual indicator 180 that signals to the user that the treatment of the room has successful. Specifically, the indicator 180 displays a signal validating the treatment of the space.

FIG. 7 depicts an exemplary apparatus of the invention. As depicted in FIG. 7, visual indicator 180 is integrated into device 140.

FIG. 8 depicts an exemplary apparatus of the invention. As depicted in FIG. 8, device 140 further comprises pump 190, optionally comprising filter 192. Pump 190 can be activated to pump air from inside the space to outside the space thereby creating negative pressure inside the space. Filter 192 allows for the operation of pump 190 during the chlorine dioxide gas generation if necessary. Filter 192 removes the chlorine dioxide gas from the air as it is pumped from inside the space to outside the space. Filter 192 can be activated charcoal, or a HEPPA filter containing sodium bisulfite or sodium sulfite. Pumps, fans and blowers, used to create negative pressure are well known in the art and commercially available.

FIG. 9 depicts an exemplary apparatus of the invention comprising multiple components described herein.

Methods of Disinfecting a Space

The instant invention provides methods and apparatus for disinfecting a space, e.g., a hospital room. Specifically, the invention provides chlorine dioxide gas generators and methods of using the same. It is understood by those of ordinary skill in the art that chlorine dioxide is a dangerous and caustic gas that must be used with care. Accordingly, the methods and apparatus of the instant invention are designed to safely disinfect a space while containing the majority of the chlorine dioxide gas.

Most rooms are not gas tight. Therefore, before disinfecting a room with chlorine dioxide gas steps must be taken to insure the safety of those in the hospital. in order to prepare a room for disinfecting with chlorine dioxide, the user may prequalify the room for treatment. This prequalification can be a one-time event that includes installing devices and hardware that limit the escape of chlorine dioxide, or may include a set up that is preformed prior to each disinfection run. For example, HVAC vents can be replaced with vents that have the ability to be sealed such that they can be closed prior to disinfection or they can be covered with a guard, e.g., a magnetic guard that is applied to the vent, prior to each treatment. Electrical receptacles, hospital specific plumbing, etc. may be sealed so as to avoid escape of chlorine dioxide gas.

Once a room is prequalified, the operator of the disinfection apparatus of the invention will set the apparatus in the room, place the door sealing device in place and begin the treatment cycle. Once the apparatus has run for a sufficient time to expose the room to the required ppm minutes of chlorine dioxide, the apparatus will engage the chlorine dioxide gas removal device in order to reduce the levels of chlorine dioxide gas in the room to a level that is safe to reenter and occupy the room, for example, less than 0.10 ppm chlorine dioxide.

Once the level is safe to reenter, the apparatus is removed from the room and optionally, the set up and/or the prequalification steps are reversed, thereby returning the room to a normal condition.

EXAMPLE 1

Disinfection of a Hospital Room

The objective is to provide methods and apparatus to safely disinfect a hospital room. The methods and apparatus do not need to completely sterilize a room, nor to kill all kinds of pathogens, but rather to sufficiently reduce the number of hospital-acquired infections (HAIs).

Current disinfection practice is to have the hospital facilities staff manually spray and/or swab the room and its contents with liquid disinfectant chemicals. It is generally recognized that manually applying chemicals is an imperfect method, and improvement is not only desired, but becoming more recognized as one important step in a multi-step program to reduce the incidence of hospital-acquired infections (HAIs).

To ensure a 90-99% reduction in a hospital room's bacterial population, microbiological tests indicate about a 15 minute treatment with an average of 6 ppm of $ClO_2$ is required. This level of $ClO_2$ is about 20 times the EPA 15-minute Permissible Exposure Limit (PEL) limit of 0.3 ppm. Therefore, people will need to be excluded during the treatment and the clearance times: Room air leakage needs to be minimized, and $ClO_2$, if present, diluted approximately 20 fold before human exposure, i.e., before humans can reenter the room after treatment.

In order to increase safety, the room should be put under negative pressure. Because hospital rooms vary in size, layout, materials of construction, HVAC design and control, windows, additional ventilation like bathroom exhaust fans, cross leaks, and quality of maintenance, a one time preparation and prequalification will be preformed. Routine disinfection then involves setup including verification of readiness for treatment, treatment, clearance, and validation of treatment.

Each phase is described in detail below. For clarity, this method will be overly specific. It is understood that this description is being used to convey understanding, rather than be precise in all the implementation details and many equivalents exist.

Prequalification—Each room to be disinfected will receive a one-time prequalification to detect and ameliorate defects and problems, and prepare the room for routine treatment. Using a negative air pressure system, major leaks are detected and sealed. This prequalification may include sealing gaps around bathroom plumbing, hospital-specific headboard plumbing and wiring, sprinkler systems, electrical outlets, recessed ceiling lights, etc. In addition, the HVAC vents and other necessary or desired apertures in the room would be prepared for rapid closure. This may include stick-on neutral or decorative magnetic strips to allow for rapid attachment and removal of magnetic covers. Moreover, a checklist of removable covers as well as any requirements that are specific to the room may be created.

Setup—The room is first prepared like it is prior to manual disinfection methods. The linens are stripped and routine cleaning is performed. The setup for disinfection may consist of placing covers on the HVAC. A computer-controlled $ClO_2$ generator is placed in the room and the inflatable bladder is placed under the door to the room. Alternatively, one of the other methods for sealing a door and placing the room under negative pressure described herein may be used. The computer on the apparatus may control a small battery-powered air pump that inflates the bladder. The bladder both seals the under-door air leakage and prevents the door from being opened while the treatment is taking place. The bladder also incorporates a differential pressure sensor comparing room pressure to corridor pressure. This sensor verifies that the room is under negative pressure, confirming all the vent covers and other preparation was correctly performed, and that the room is ready for treatment. The bladder may also comprise a visual indicator that indicates when the room is under negative pressure:

Treatment—When the setup is complete, the operator leaves the room, closes the door and starts the treatment process. Once the process has begun, the computer inflates the bladder and verifies that there is sufficient pressure in the bladder and a negative differential pressure between the corridor and room sides of the bladder. If the computer detects a problem, i.e., that the room is not under negative pressure, the chlorine dioxide gas generator will not begin to generate chlorine dioxide gas. If no problem is detected, the computer turns on the chlorine dioxide gas generator. The computer monitors the chlorine dioxide gas level in the room and a servo controls the chlorine dioxide gas level to provide the correct treatment dosage. The computer makes a record of the chlorine dioxide gas level in the room and the generator duty cycle that indicates the chlorine dioxide gas demand of the room.

Clearance—Once the room is exposed to sufficient levels of chlorine dioxide gas for sufficient time, the computer turns off the chlorine dioxide gas generator, and continues to monitor the chlorine dioxide gas level in the room. If chlorine dioxide gas is present above the re-entry level, the computer turns on the chlorine dioxide gas scrubber. When the room is safe to enter, the computer deflates the bladder and allows for reentry to the room. The scrubber may comprise a HEPPA filter containing sodium bisulfite or sodium sulfite and a fan.

Validation of treatment—The time record of chlorine dioxide gas room concentration validates that the correct concentration time profile, or PPM minutes, was obtained to disinfect the room. A second chlorine dioxide gas sensor may be used at a location remote from the chlorine generator to validate that the entire space was adequately disinfected. This battery-powered sensor wirelessly communicates with the computer. The validation data can be wirelessly communicated to the hospital records computer, confirming that the treatment took place and was verified to fall within the anticipated operating parameters. The validation process runs concurrently with the overall disinfection processes and does not add any additional process time.

EXAMPLE 2

Test Results

Disinfection of hospital rooms was done in cooperation with Massachusetts General Hospital and an EPA/FDA approved laboratory. The effectiveness of chlorine dioxide gas on selected target microorganisms with low doses of chlorine dioxide gas was evaluated. The effectiveness of chlorine dioxide, or any chemical disinfectant, is related to a combination of concentration and time. The test results below indicate 90-99% reduction in selected microorganisms, including MRSA and VRE, can be achieved with dose levels as low as 0.63 ppm.

TABLE 1

2.4 ppm Dose of $ClO_2$ for 26 Minutes
(62 ppm-min) - $10^6$ Starting Organisms

| Organism | % Reduction |
| --- | --- |
| S. aureus | >99.9% |
| Pseudomonas aeruginosa | >99.99% |
| Salmonella | 99.9999% |

TABLE 2

2.1 ppm Dose of $ClO_2$ for 22 Minutes
(47 ppm-min) - $10^3$ Starting Organisms

| Organism | % Reduction |
| --- | --- |
| S. aureus | ~99% |
| E. coli | >99% |
| Enterococcus faecalis | >99% |

TABLE 3

21 ppm Dose of $ClO_2$ for 16 Minutes (336 ppm-min) - $10^3$ Starting Organisms

| Organism | % Reduction |
| --- | --- |
| S. aureus | >99% |
| E. coli | >99% |

TABLE 3-continued 21 ppm Dose of $ClO_2$ for 16 Minutes (336 ppm-min) - $10^3$ Starting Organisms

| Organism | % Reduction |
| --- | --- |
| Enterococcus faecalis | >99% |
| Pseudomonas aeruginosa | >99% |

TABLE 4

0.63 ppm Dose of $ClO_2$ for 14 Minutes
(9 ppm-min) - $10^3$ Starting Organisms

| Organism | % Reduction |
| --- | --- |
| E. coli | ~98% |
| Enterococcus faecalis | ~90% |

Based on the foregoing examples, it is apparent the methods and apparatus described herein are effective for significantly reducing the number of microorganisms in hospital rooms.

INCORPORATION BY REFERENCE

The contents of all references, patents, pending patent applications, and published patents cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the instant invention and the following claims.

What is claimed is:

1. A method of disinfecting a space comprising:
providing an apparatus for disinfecting a space, the apparatus comprising:
a chlorine dioxide gas generator;
a sealing device comprising a sensor configured to measure pressure inside and outside of the space; and
a computer operatively connected to the sensor and the chlorine dioxide generator;
preparing the space to receive a chlorine dioxide gas to disinfect the space;
determining if the space is under a negative pressure;
generating the chlorine dioxide gas to disinfect the space if the space is under negative pressure; and
validating a concentration profile and a duration profile to verify disinfection of the space.

2. The method of claim 1, further comprising: selecting a sealing device from a group comprising, an inflatable bladder, an inflatable door, a compressible foam insert for under the door or a sheet that covers an outside of the doorway.

3. The method of claim 1, further comprising: attaching a sealing device to the exterior of a door frame.

4. The method of claim 1, further comprising: configuring the concentration profile and the duration profile to operate concurrently with the generation of the chlorine dioxide gas to disinfect the space.

5. The method of claim 1, further comprising: configuring a compressor to inflate the sealing device.

6. The method of claim 1, further comprising: configuring an air circulation device for circulation of the chlorine dioxide gas.

7. The method of claim 1, further comprising: utilizing the sealing device to prevent entry into the space.

8. The method of claim 1, further comprising: utilizing a visual indicator to indicate safe entry into the space.

9. The method of claim 1, further comprising: configuring a visual indicator to indicate negative pressure.

10. The method of claim 1, further comprising: configuring a negative pressure pump.

11. The method of claim 1, further comprising: integrating a negative pressure pump into the sealing device.

12. The method of claim 10, further comprising: integrating a filter to remove the chlorine dioxide gases.

13. The method of claim 1, wherein the space is a hospital room.

14. The method of claim 1, wherein the space is a nursing home room.

15. The method of claim 1, further comprising: sealing an HVAC duct prior to generation of the chlorine dioxide gas.

16. The method of claim 1, further comprising: sealing an electrical outlet prior to generation of the chlorine dioxide gas.

17. The method of claim 1, further comprising: sealing an electronic device prior to generation of the chlorine dioxide gas.

18. The method of claim 1, further comprising: configuring the apparatus to receive a machine-readable identification information from a removable precursor chemical cartridge.

19. The method of claim 1 further comprising: configuring a selectively detachable display to the chlorine dioxide gas generator for disinfecting a space.

20. The method of claim 19, further comprising: configuring wireless communication between the selectively detachable display and the chlorine dioxide gas generator.

21. The method of claim 1, further comprising: configuring a second chlorine dioxide gas sensor to operate remotely from the chlorine dioxide gas generator.

22. The method of claim 1, further comprising: configuring the second chlorine dioxide gas sensor to signal the computer to turn off the chlorine dioxide gas generator.

23. The method of claim 21, further comprising: configuring the second chlorine dioxide gas sensor to verify disinfection of the space.

24. The method of claim 1, further comprising: configuring the sensor to signal the computer to turn off the chlorine dioxide gas generator.

25. The method of claim 1, further comprising: un-sealing an HVAC duct after the generation of the chlorine dioxide gas.

26. The method of claim 1, further comprising: re-sealing an HVAC duct after the generation of the chlorine dioxide gas.

27. The method of claim 1, further comprising: pre-qualifying the space to receive the chlorine dioxide gas to disinfect the space.

28. The method of claim 1, further comprising: disinfecting the space in under three hours.

29. The method of claim 1, further comprising: disinfecting the space in under one hours.

* * * * *